United States Patent
Spielvogel et al.

(10) Patent No.: US 7,524,477 B2
(45) Date of Patent: Apr. 28, 2009

(54) METHOD OF PRODUCTION OF $B_{10}H_{10}^{2-}$ AMMONIUM SALTS AND METHODS OF PRODUCTION OF $B_{18}H_{22}$

(75) Inventors: Bernard Spielvogel, Hubbards (CA); Kevin Cook, Hammonds Plains (CA)

(73) Assignee: SemEquip Inc., N. Billerica, MA (US)

( * ) Notice: Subject to any disclaimer, the term of this patent is extended or adjusted under 35 U.S.C. 154(b) by 451 days.

(21) Appl. No.: 11/050,159

(22) Filed: Feb. 2, 2005

(65) Prior Publication Data

US 2005/0169828 A1 Aug. 4, 2005

Related U.S. Application Data

(60) Provisional application No. 60/541,322, filed on Feb. 2, 2004.

(51) Int. Cl.
*C01B 6/10* (2006.01)
*C07F 5/02* (2006.01)

(52) U.S. Cl. ............................. 423/294; 423/283; 564/8

(58) Field of Classification Search .................. 423/294, 423/283; 564/8
See application file for complete search history.

(56) References Cited

U.S. PATENT DOCUMENTS

| | | | |
|---|---|---|---|
| 2,642,453 A | 6/1953 | Lippincott et al. |
| 3,063,791 A | 11/1962 | Kollinitsch et al. |
| 3,489,517 A | 1/1970 | Shore et al. |
| 4,026,993 A | 5/1977 | Ditter et al. |
| 4,115,520 A | 9/1978 | Dunks et al. |
| 4,115,521 A | 9/1978 | Dunks et al. |
| 4,153,672 A | 5/1979 | Dunks et al. |
| 4,338,289 A | 7/1982 | Shore et al. |
| 4,391,993 A | 7/1983 | Sayles |

(Continued)

FOREIGN PATENT DOCUMENTS

WO    WO-03/044837 A2    5/2003

(Continued)

OTHER PUBLICATIONS

Mangeot et al, "$(Et_4N)_2B_{10}H_{10}$ and $(Et_4N)_2B_{12}H_{12}$; synthesis from $Et_4$, $NBH_4$, separation and purification", Bulletin de la Socite Chimique de France (3), 385-9 (French) 1986 no month.*

(Continued)

*Primary Examiner*—Wayne Langel
(74) *Attorney, Agent, or Firm*—Peter F. Corless; Edwards Angell Palmer & Dodge LLP

(57) ABSTRACT

The invention provides new methods for synthesis of $B_9H_9^-$, $B_{10}H_{10}^{2-}$, $B_{11}H_{14}^-$, and $B_{12}H_{12}^{2-}$ salts, particularly alkylammonium salts of $B_9H_9^-$, $B_{10}H_{10}^{2-}$, $B_{11}H_{14}^-$, and $B_{12}H_{12}^{2-}$. More particularly, the invention provides methods of preparing tetraalkylamronium salts of $B_9H_9^-$, $B_{10}H_{10}^{2-}$, $B_{11}H_{14}^-$, and $B_{12}H_{12}^{2-}$ by pyrolysis of tetraalkylammonium borohydrides under controlled conditions. The invention additionally provides methods of preparing, in an atom efficient process, octadecaborane from the tetraalkylammonium salts of the invention. Preferred methods of the invention are suitable for preparation of isotopically enriched boranes, particularly isotopically enriched $^{10}B_{18}H_{22}$ and $^{11}B_{18}H_{22}$.

15 Claims, 1 Drawing Sheet

U.S. PATENT DOCUMENTS 6,086,837 A 7/2000 Cowan et al.

FOREIGN PATENT DOCUMENTS

WO WO-2004/003973 A2 1/2004

OTHER PUBLICATIONS

Y. Kawasaki et al. "Ultra-Shallow Junction Formation by $B_{18}H_{22}$ Ion Implantation" Presented at: Ion Implantation Technology 2004, Oct. 24-29, 2004, Taipe, Taiwan.

L. Adams et al. "A New Synthetic Route to Boron-10 Enriched Pentaborane(9) from Boric Acid and its Conversion to anti-$^{10}B_{18}H_{22}$," *Journal of the American Chemical Society* 2002, 124, 7292-7293, no month.

E.D. Jemmis et al. "Electronic Requirements for Macropolyhedral Boranes" *Chemical Reviews* 2002, 102, 93-144, no month.

E.D. Jemmis et al. "A Unifying Electron-Counting Rule for Macropolyhedral Boranes, Metallaboranes, and Metallocenes" *Journal of the American Chemical Society*, 2001, 123, 4313-4123, no month.

H. Mongeot et al. "(ET4N)2B10H10 et (ET4N)2B12H12: Synthese de Et4NBH4, Separation et Purification" Bulletin De La Societe Chimique De France 1986, 3, 358-389, no month.

D.F. Gaines et al. "Preparation of $n$—Octadecaborane(22), $n\ B_{18}H_{22}$, by Oxidative Fusion of Dodecahydrononaborane(1-) Clusters", no date.

A. Ouassas et al., Etude de la synthese des ions decahydrodecaborate(-2) B10H102- et dodecahydrodecaborate(-2) B12H122- Bulletin De La Societe Chimique De France 1984, 3, 1-336-389, no month.

N.N. Greenwood et al. *Chemistry of the Elements*, Chapter 6, Butterworth-Heinemann, Oxford, UK (1984), no month.

D. H. Gibson et al. "Reductions of Metal Carbonyls by Quaternary Ammonium Borohydrides" Journal of Ogranometallic Chemistry 1981, 218, 325-336, no month.

G. B. Dunks et al. "Simplified Synthesis of B10H14 from NaBH4 via the B11H14-Ion" Inorganic Chemistry 1981, 20, 1962-1697, no month.

W. E. Hill et al. "From Sodium Borohydride to 1,2-dicarba-closo-dodecabomes" in Boron Chemistry 1979, 33-39, no month.

G. B. Dunks et al. "A One-Step Synthesis of B11H14-from NaBH4" Inorganic Chemistry 1978, 17, 1514-1516, no month.

R. K. Hertz et al. "Quartenacy Ammonium and Phosphonium Heptahydrodiborates" Inorganic Syntheses, 1977, 17, 21, no month.

L.L. Ingram et al. "Mass Spectrum of $n$—Octadecaborane, $n$—$B_{18}H_{22}$" *Spectroscopy Letters*, 1975, 8, 483, no month.

A. Brandstrom et al. "An Improved Method for the Preparation of Solutions of Diborane" TetrahedronbLetters 1972, 31, 3173-3176, no month.

J.S. McAvoy et al. "The Preparation of n-$B_{18}H_{22}$ via the Protonolysis of the Tetradecahydroundecaborate Ion, $B_{11}H_{14}$-" *Chemical Communications* 1969, 1378-1379, no month.

F.P. Olsen et al. "The Chemistry of $n$—$B_{18}H_{22}$ and $i$—$B_{18}H_{22}$" *Journal of the American Chemical Society* 1968, 90, 3946-3951, no month.

M.F. Hawthorne et al. "The Preparation and Rearrangement of the Three Isomeric $B_{20}H_{18}^{4-}$—Ions" *Journal of the American Chemical Society* 1965, 87, 1893, no month.

J. Plesek et al. "Chemistry of Boranes. VII. A New Synthesis of Borane $B_{18}H_{22}$; An Application of Three-Center Bonds Theory on the Interpretation of Reaction Mechanisms" *Coll. Czech. Chem. Commun.* 1967, 32, 1095-1103, no month.

M.F. Hawthorne et al. "Bis(triethylammonium) Decahydrodecaborate(2-)" vol. IX, *Inorganic Syntheses*, Edited by S Young Tyree, Jr., McGraw-Hill Publishing Co., Inc., New York, New York (1967), 16-19, no month.

E.L. Chamberland et al. "Chemistry of Boranes. XVIII. Oxidation of $B_{10}H_{10}^{-2}$ and Its Derivatives" *Inorganic Chemistry* 1964, 3, 1450-1456, no month.

P.G. Simpson et al. "Molecular, Crystal, and Valence Structures of $B_{18}H_{22}$" *J. Chem. Phys.* 1963, 39, 26, no month.

P.G. Simpson et al. "Molecular, Crystal, and Valence Structures of $Iso$-$B_{18}H_{22}$" *J. Chem. Phys.* 1963, 39, 2339, no month.

A.R. Pitochelli et al. "The Preparation of a New Boron Hydride $B_{18}H_{22}$" *Journal of the American Chemical Society* 1962, 84, 3218, no month.

A. Kaczmarczyk et al. "Reactions of $B_{10}H_{10}^{2-}$ Ion" *Proceedings of the National Academy of Sciences of the United States of America* 1962, 48, 729-733, no month.

M.F. Hawthorne et al. "The Reactions of Bis-Acetonitrile Decaborane with Amines" *Journal of the American Chemical Society* 1959, 81, 5519, no month.

H. Steinberg et al. "Preparation and Rate of Hydrolysis of Boric Acid Esters" Industrial and Engineering Chemistry, 1957, 49, 174, no month.

\* cited by examiner

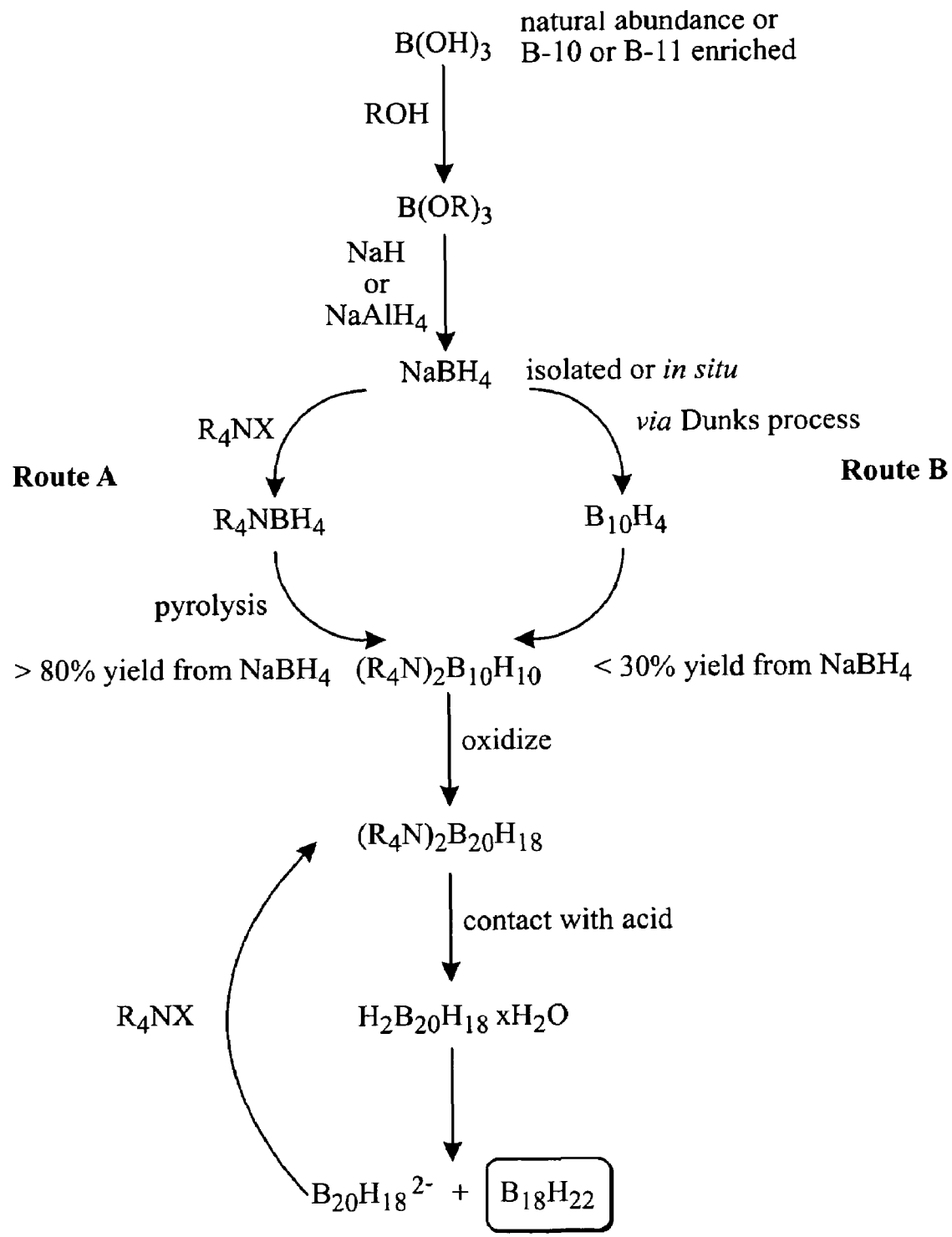

METHOD OF PRODUCTION OF $B_{10}H_{10}^{2-}$ AMMONIUM SALTS AND METHODS OF PRODUCTION OF $B_{18}H_{22}$

CROSS-REFERENCE TO RELATED APPLICATION(S)

This application claims priority from U.S. Provisional Patent Application 60/541,322 which was filed on Feb. 2, 2004, which is incorporated by reference.

FIELD OF THE INVENTION

The invention provides methods for synthesizing borane compounds comprising pyrolysis of ammonium borohydride compounds under controlled thermal conditions. The invention further provides isotopically enriched boron compounds prepared by the aforementioned methods. In certain aspects, the invention relates to methods of preparing $B_{18}H_{22}$, including $^{10}B$- and $^{11}B$-enriched $B_{18}H_{22}$, and methods of preparing salts of $B_9H_9^-$, $B_{10}H_{10}^{2-}$, $B_{11}H_{14}^-$, and $B_{12}H_{12}^{2-}$.

BACKGROUND OF THE INVENTION

Large boron hydride compounds have become important feed stocks for boron doped P-type impurity regions in semiconductor manufacture. More particularly, high molecular weight boron hydride compounds, e.g., boron hydride compounds comprising at least a five (5) boron atom cluster, are preferred boron atom feed stocks for boron atom implantation.

An important aspect of modern semiconductor technology is the continuous development of smaller and faster devices. This process is called scaling. Scaling is driven by continuous advances in lithographic process methods, allowing the definition of smaller and smaller features in the semiconductor substrate which contains the integrated circuits. A generally accepted scaling theory has been developed to guide chip manufacturers in the appropriate resize of all aspects of the semiconductor device design at the same time, i.e., at each technology or scaling node. The greatest impact of scaling on ion implantation processes is the scaling of junction depths, which requires increasingly shallow junctions as the device dimensions are decreased. This requirement for increasingly shallow junctions as integrated circuit technology scales translates into the following requirement: ion implantation energies must be reduced with each scaling step. The extremely shallow junctions called for by modern, sub-0.13 micron devices are termed "Ultra-Shallow Junctions" or USJs.

Methods of manufacturing boron doped P-type junctions have been hampered by difficulty in the ion-implantation process using boron. The boron atom, being light (average atomic weight of 10.8), can penetrate more deeply into a silicon substrate and diffuse throughout the substrate lattice rapidly during annealing or other elevated temperature processes.

Boron clusters or cages, e.g., boranes have been investigated as a feed stock for delivering boron to a semiconductor substrate with reduced penetration. For example, as recited in commonly assigned International Patent Application PCT/US03/20197 filed Jun. 26, 2003, boron ions may be implanted into a substrate by ionizing boron hydride molecules of the formula $B_nH_m$ (where 100>n>5 and m≦n+8) and an ion source for use in said implantation methods. Certain preferred compounds for use in the boron ion implantation methods included decaborane ($B_{10}H_{14}$) and octadecaborane ($B_{18}H_{22}$).

A typical molecular ion beam of $B_{18}H_{22}$ contains ions of a wide range of masses due to loss of a varying number of hydrogens from the molecular ion as well as the varying mass due to the two naturally occurring isotopes. Because mass selection is possible in an implanter device used in semiconductor manufacture, use of isotopically enriched boron in $B_{18}H_{22}$ can greatly reduce the spread of masses, thereby providing an increased beam current of the desired implantation species. Thus, B-11 and B-10 isotopically-enriched $B_{18}H_{22}$ is also of great interest.

$B_{18}H_{22}$ can be prepared by the oxidation of alkylammonium salts of the $B_{10}H_{10}$ dianion. Preparation of this dianion can be accomplished in high yield from decaborane (M. F. Hawthorne and A. R. Pitochelli J. Am. Chem. Soc. 81, 5519, 1959.). However decaborane is toxic, expensive and difficult to prepare by reported synthetic procedures (see, U.S. Pat. No. 4,115,521, issued to Dunks et al.). More particularly, the Dunks method of synthesis of decaborane employs costly solvents and reagents, time consuming reaction conditions, and often laborious work up procedures. Thus, the overall yield for the preparation of salts of the $B_{10}H_{10}$ dianion starting from sodium borohydride and proceeding through decaborane is typically below 30%.

Preparation of B-10 and B-11 enriched salts of the $B_{10}H_{10}$ dianion, and preparation of large boron hydrides from salts of the $B_{10}H_{10}$ dianion (such as $B_{18}H_{22}$), via enriched decaborane is a particularly expensive process in part because substantial quantities of preparation of B-10 or B-11 enriched from sodium borohydride is diverted to byproducts instead of incorporation into the enriched decaborane and enriched $B_{10}H_{10}^{2-}$ dianion.

International patent application WO 03/044837, (Applied Materials, Inc, Santa Clara Calif.) recites methods of ion implantation in which an isotopically enriched boron compounds including $^{11}B$ enriched compounds are ionized and then implanted into a substrate. The '837 publication recites the preparation of the iosotopically enriched boranes by the method recited in U.S. Pat. No. 6,086,837 (Cowan, et al.), which methods are reported to be the current industrial process for the preparation of boranes isotopically enriched in $^{10}B$ or $^{11}B$.

Cowan (U.S. Pat. No. 6,086,837) recites a method of preparing B-10 enriched decaborane starting with B-10 enriched boric acid. The Cowan preparation of either B-10 or B-11 enriched boron hydrides begins with boric acid and involves a multitude of synthetic and purification steps. More particularly, the Cowan process for conversion of boric acid into an alkali metal borohydride involves numerous time consuming steps and results in a relatively low yield of valuable B-10 enriched borohydride which must then be subjected to further reactions to obtain final product.

Thus, the Cowan method starts with the preparation of B-10 methylborate from boric acid and methanol using an azeotropic distillation method. The methylborate is separated from remaining methanol by freeze recrystallization by means of three one step procedures to produce an 80% yield of trimethylborate. The trimethylborate is then added to a suspension of sodium hydride in mineral oil at 220° C.-250° C. and heated for 12 hrs. For safety, a metal reflux condenser is required. Isolation of the formed borohydride requires special attention. First, the excess sodium hydride is destroyed by pouring the mineral oil mixture into a mixture of ice and water, a rather exothermic process evolving gaseous hydrogen. Then the aqueous borohydride is separated from the mineral oil by decantation or use of separatory funnel. The aqueous borohydride must be purged of methanol by either heating to 60° C. and purged with a nitrogen stream or by removal under reduced pressure. The resulting aqueous solution is comprised of sodium hydroxide and the B-10 enriched borohydride. Carbon dioxide gas is bubbled through the solution converting the sodium hydroxide to sodium carbonate. The resulting slurry is then extracted with n-propylamine and the n-propylamine evaporated to yield final product. The solubilty of sodium borohydride in n-propylamine is limited and appreciable volumes of the volatile solvent are needed. Typical yields of 45-65% are obtained. A total of ten time consuming steps are required to prepare isotopically enriched sodium borohydride by the procedure recited in Cowan.

Several literature documents recite conflicting synthetic reports regarding the preparation of salts of the $B_{10}H_{10}^{2-}$ anion from tetralkylammonium borohydride salts. The literature recites conducting the pyrolysis in a variety of reactors, in the presence or absence of a solvent, and under a variety of reaction conditions. See, for example, (1) W. E. Hill et al, "Boron Chemistry 4." Pergamon Press, Oxford 1979, p 33; (2) Mongeot et al Bull. Soc. Chim. Fr. 385, 1986; and (3) U.S. Pat. Nos. 4,150,057 and 4,391,993, issued to Sayles. The published procedures do not provide the means for industrially significant production of the $B_{10}H_{10}^{2-}$ anion, predictable and consistent conversion to product are not taught, and purification techniques are inadequate for the intended use.

Several reports have recited processes for the preparation of naturally abundant tetraalkylammonium borohydride compounds from sodium borohydride. However, the literature methods are not suitable for preparation of isotopically enriched ammonium borohydrides, in part because, a substantial amount of the borohydride is sacrificed during cation exchange. For example, Gibson and Shore separately recite contacting two equivalents of sodium borohydride with a mixture of tetraethylammonium hydroxide and sodium hydroxide in methanol to generate one equivalent of tetraethylammonium borohydride, which may be contaminated with sodium hydroxide (D. Gibson et al, J. Organornet. Chem, 218, 325, 1981; and S. Shore et al., Inorg. Synth. 17, 21, 1977). Due to the stoichometric loss of boron, these processes are not suitable for preparation of B-10 or B-11 enriched tetraalkylammonium borohydride salts.

Brändström et al recites methods of synthesis of tetralkylammonium borohydride compounds containing 12 or more carbon atoms from tetraalkylammonium hydrogen sulfate and a 10% excess of sodium borohydride (Brändström et al Tet. Lett. 31, 3173, 1972). Notwithstanding the quantitative conversion to the desired production solution, Applicants attempts to isolate the product tetralkylammonium borohydride from solution were plagued by unsatisfactory isolated yields and development of viscous "oils" that were difficult to crystallize and purify following the recited procedure.

It would be desirable to have a reproducible, atom-efficient, high-yielding process for preparing high-purity salts of the $B_{10}H_{10}^{2-}$ dianion from borohydride precursors. More particularly, it would be desirable to have methods of preparing high purity natural abundant, B-10 enriched, or B-11 enriched salts of $B_{10}H_{10}^{2-}$, which methods have a reduced number of synthetic procedures.

SUMMARY OF THE INVENTION

We have discovered a new method of synthesis of alkylammonium salts of the $B_{10}H_{10}$ dianion. More particularly, we have discovered an atom efficient, high yield method of synthesis of alkylammonium salts of $B_{10}H_{10}^{2-}$, which methods do not include formation of decaborane as an intermediate. The methods of the invention generally comprise the preparation of a tetraalkylammonium borohydride from sodium borohydride and pyrolysis of the alkylammonium borohydride to generate an alkylammonium salt of $B_{10}H_{10}^{2-}$. The methods of the invention are suitable for use in preparing naturally abundant, B-10 enriched and B-11 enriched alkylammonium salts of the $B_{10}H_{10}^{2-}$ dianion.

In one aspect, the invention provides a method of preparing an alkylammonium salt of $B_{10}H_{10}$ dianion, the method comprising the steps of:
 (a) contacting a boric acid and a primary, secondary, or tertiary alcohol under conditions conducive to formation of a borate ester;
 (b) reducing the borate ester with $NaAlH_4$ or $NaH$ to form $NaBH_4$; and
 (c) contacting $NaBH_4$ with an alkylammonium salt of the formula, $R_4NX$, where R is a linear or branched alkyl group or an aralkyl group under conditions conducive to formation of either in situ or after isolation of $R_4NBH_4$; and
 (d) pyrolysis of solid $R_4NBR_4$ at about 185° C. to form an ammonium salt of $B_{10}H_{10}^{2-}$.

In another aspect, the invention provides methods of preparing $B_{18}H_{22}$, the method comprising the steps of:
 (a) contacting boric acid with a primary, secondary, or tertiary alcohol under conditions conducive to borate ester formation;
 (b) reducing the borate ester with a metal hydride or metal hydride salt to afford a metal borohydride;
 (c) contacting the metal borohydride with a salt of the formula $R_4NX$, wherein R is a hydrocarbon group and X is an anion to afford $R_4NBH_4$;
 (d) heating solid $R_4NBH_4$ at a temperature sufficient to selectively form a salt of the $B_{10}H_{10}^{2-}$ anion during pyrolysis;
 (e) contacting the salt of the $B_{10}H_{10}^{2-}$ anion with an oxidant under conditions conducive to formation of a salt of $B_{20}H_{18}^{2-}$;
 (f) contacting the $B_{20}H_{18}^{2-}$ salt in its free form, as a slurry in at least one non-aqueous solvent, as an aqueous solution, or as a solution in at least one non-aqueous solvent with an acid under conditions conducive to the formation of a conjugate acid of the $B_{20}H_{18}^{2-}$ salt;
 (g) removing volatile components of the solution comprising the conjugate acid of the $B_{20}H_{18}^{2-}$ salt under conditions conducive to the degradation of at least a portion of the conjugate acid of the $B_{20}H_{18}^{2-}$ salt;
 (h) extracting the residue with hexanes or other suitable hydrocarbon solvents in which boric acid byproduct is insoluble;
 (i) repeating steps (g) and (h) until no further $B_{18}H_{22}$ is produced;
 (j) contacting the residues with solvent to dissolve any $B_{20}H_{18}^{2-}$ containing salts;
 (k) repeating steps (f)-(j) at least once; and
 (l) concentrating the combined hydrocarbon solutions to afford $B_{18}H_{22}$.

In another aspect, the invention provides methods of preparing $^{11}$B-enriched $B_{18}H_{22}$, the method comprising the steps of:
 (a) contacting boric acid with a primary, secondary, or tertiary alcohol under conditions conducive to borate ester formation;
 (b) reducing the borate ester with a metal hydride or metal hydride salt to afford a metal borohydride;
 (c) contacting the metal borohydride with a salt of the formula $R_4NX$, wherein R is a hydrocarbon group and X is an anion to afford $R_4NBH_4$;

(d) heating solid $R_4NBH_4$ at a temperature sufficient to selectively form a salt of the $B_{10}H_{10}^{2-}$ anion during pyrolysis;

(e) contacting the salt of the $B_{10}H_{10}^{2-}$ anion with an oxidant under conditions conducive to formation of a salt of $B_{20}H_{18}^{2-}$;

(f) contacting the $B_{20}H_{18}^{2-}$ salt in its free form, as a slurry in at least one non-aqueous solvent, as an aqueous solution, or as a solution in at least one non-aqueous solvent with an acid under conditions conducive to the formation of a conjugate acid of the $B_{20}H_{18}^{2-}$ salt;

(g) removing volatile components of the solution comprising the conjugate acid of the $B_{20}H_{18}^{2-}$ salt under conditions conducive to the degradation of at least a portion of the conjugate acid of the $B_{20}H_{18}^{2-}$ salt;

(h) extracting the residue with hexanes or other suitable hydrocarbon solvents in which boric acid byproduct is insoluble;

(i) repeating steps (g) and (h) until no further $B_{18}H_{22}$ is produced;

(j) contacting the residues with solvent to dissolve any $B_{20}H_{18}^{2-}$ containing salts;

(k) repeating steps (f)-(j) at least once; and (l) concentrating the combined hydrocarbon solutions to afford $B_{18}H_{22}$.

In another aspect, the invention provides methods of preparing $^{10}$B-enriched $B_{18}H_{22}$, the method comprising the steps of:

(a) Contacting a boric acid and a primary, secondary, or tertiary alcohol under conditions conducive to borate ester formation;

(b) reducing the borate ester with a metal hydride or metal hydride salt to afford a metal borohydride;

(c) contacting the metal borohydride with a salt of the formula $R_4NX$, wherein R is a hydrocarbon group and X is an anion to afford $R_4NBH_4$;

(d) heating solid $R_4NBH_4$ at a temperature sufficient to selectively form a salt of the $B_{10}H_{10}^{2-}$ anion during pyrolysis;

(e) contacting the salt of the $B_{10}H_{10}^{2-}$ anion with an oxidant under conditions conducive to formation of a salt of $B_{20}H_{18}^{2-}$;

(f) contacting the $B_{20}H_{18}^{2-}$ salt in its free form, as a slurry in at least one non-aqueous solvent, as an aqueous solution, or as a solution in at least one non-aqueous solvent with an acid under conditions conducive to the formation of a conjugate acid of the $B_{20}H_{18}^{2-}$ salt;

(g) removing volatile components of the solution comprising the conjugate acid of the $B_{20}H_{18}^{2-}$ salt under conditions conducive to the degradation of at least a portion of the conjugate acid of the $B_{20}H_{18}^{2-}$ salt;

(h) extracting the residue with hexanes or other suitable hydrocarbon solvents in which boric acid byproduct is insoluble;

(i) repeating steps (g) and (h) until no further $B_{18}H_{22}$ is produced;

(j) contacting the residues with solvent to dissolve any $B_{20}H_{18}^{2-}$ containing salts;

(k) repeating steps (f)-(j) at least once; and (l) concentrating the combined hydrocarbon solutions to afford $B_{18}H_{22}$.

Other aspects of the invention are discussed infra.

BRIEF DESCRIPTION OF THE DRAWINGS

We first briefly describe the drawings of the preferred embodiment of the invention.

The FIGURE is a flow chart of a synthetic method of preparing $B_{18}H_{22}$ by a method of the present invention (Route A) and a method of preparing $B_{18}H_{22}$ using the Dunks process to prepare $(NR_4)_2B_{10}H_{10}$ (Route B).

DETAILED DESCRIPTION OF THE INVENTION

Remarkably, we have discovered new methods for the preparation of ammonium salts of anionic boron hydrides having between 9 and 12 boron atoms from various ammonium borohydrides. We have also discovered new methods of preparing boron hydrides, including $B_{18}H_{22}$ and related large boron hydride compounds, which can be useful as feed stocks for methods of implanting boron atoms in a substrate by molecular ion implantation.

Now referring to the FIGURE, certain preferred methods of synthesizing $B_{18}H_{22}$ provided by the invention are depicted in Route A. In contrast, the synthetic procedure of Route B refers to certain methods of making $B_{18}H_{22}$ using the Dunks procedure to make ammonium decaborane salts.

Enriched tetraalkylammonium borohydride salts can be obtained by the preparation of enriched sodium borohydride through the following steps:

(a) B-11 or B-10 enriched boric acid is converted to an organic ester which can be prepared from a wide variety of alcohols, glycols, and phenols. See, for example Steinberg and Hunter, J. of Industrial and Engineering Chemistry, Vol 49, 174-181. Generally, selection of alcohol, glycol, or phenol is made on the basis of cost and availability of the esterifying agent and ease of preparation. Certain non-limiting examples of suitable alcohols and glycols include n-butanol and 2-methyl-2,4-pentanediol. Typically glycols generate a tri(glycolate)bisborate structure in high yield, e.g., tri(2-methyl-2,4-pentanediolate)bisborate can be prepared in essentially quantitative yield.

(b) The borate ester is reduced directly to B-11 or B-10 enriched alkali metal borohydride using alkali metal hydrides such as sodium aluminum hydride. Preferable is the use of sodium aluminum hydride in tetrahydrofuran (THF) and/or diethylether which may further comprise toluene as a cosolvent. Addition of toluene as a co-solvent may be desirable in certain embodiments, in part because the use of toluene reduces the risks associated with the use of ethereal solvents.

(c) The B-11 or B-10 enriched metal borohydride salts prepared in step (b) are of sufficient purity to proceed with the production of enriched tetraalkylammonium borohydride.

Tetraalkylammonium borohydride salts $(R_4N^{30}BH_4^-)$ are prepared by contacting sodium borohydride with one or more molar equivalents of a tetralkylammonium salt such as tetralkylammonium hydrogensulfate, or the like, in an aqueous or alcohol solution. Sodium hydroxide or the like is then added to the reaction mixture to generate a basic reaction mixture. When an aqueous reaction medium is used, the aqueous solution is extracted with methylene chloride in a biphasic extraction. Alternatively, when an alcohol solvent is used, the alcohol is evaporated and the residue extracted with methylene chloride. After drying, the methylene chloride solution is concentrated to afford a viscous solution. Addition of diethylether to the concentrated methylene chloride solution results in precipitation of the borohydride salt in high yield. Alternatively, when the methylene chloride can be removed completely and the crude solid recrystallized from ethyl acetate albeit in lower isolated yield.

The invention provides methods of production of tetraalkylammonium salts of the $B_{10}H_{10}^{2-}$ dianion by pyrolysis of at least one tetraalkylammonium borohydride. Certain preferred pyrolytic methods of the invention are scalable for large scale synthesis of tetraalkylammonium salts of $B_{10}H_{10}^{2-}$. The pyrolysis reaction can be performed using the solid tetraalkylammonium borohydride or as a slurry of the tetraalkylammonium borohydride in a hydrocarbon solvent having a boiling point of at least 100° C. Certain preferred hydrocarbon solvents include alkane solvents having between 8 and 18 carbon atoms.

Pyrolysis reactions of the invention are preferably conducted in a reaction apparatus that has ports to allow the vessel to be evacuated and/or to allow for introduction of an inert atmosphere (e.g., nitrogen, argon, or the like). In addition, preferred pyrolysis reaction apparatus comprise a vent port to transfer gaseous byproducts to an appropriate scrubber.

Careful regulation of the temperature of the reaction mixture during pyrolysis improves control of the composition and purity of the product mixture. Thus, preferred reactors permit precise temperature control. More preferably, the apparatus comprises a thermowell or the like to take precise internal temperature readings, an external furnace or other heat source that delivers even heating to the reaction, a method of cooling the reaction mixture that prohibits overheating while maximizing temperature control, and a temperature control unit that can maintain a temperature program containing multiple "ramp" and "soak" events. Pyrolysis of a tetraalkylammonium borohydride in this reaction vessel provided good to high yields of tetraalkylammonium salts of $B_{10}H_{10}^{2-}$, $B_9H_9^-$, $B_{11}H_{14}^-$ and $B_{12}H_{12}^{2-}$ by regulating the temperature profile of the reaction vessel during pyrolysis.

The reaction apparatus further permits incorporation of additional reagents (such as trialkylamine borane adducts) and/or solvents in order to achieve the optimum production of a specified boron hydride anion (e.g., $B_{10}H_{10}^{2-}$, $B_9H_9^-$, $B_{11}H_{14}^-$ and $B_{12}H_{12}^{2-}$). Yields up to 90% for $B_{10}H_{10}^{2-}$ or $B_{12}H_{12}^{2-}$ have been obtained by the methods of the invention. From $NaBH_4$, the overall yield for tetraalkylammonium salts of $B_{10}H_{10}^{2-}$ can be greater than 80%, which is substantially greater than yields obtained by synthetic procedures using decaborane as an intermediate (i.e., by the Dunks process which provides overall yields of less than 30%).

In certain preferred methods of preparing salts of $B_{10}H_{10}^{2-}$, $B_9H_9^-$, $B_{11}H_{14}^-$ and/or $B_{12}H_{12}^{2-}$, the $R_4NBH_4$ is dissolved, suspended or mixed with a solvent having a boiling point of at least about 100° C. Certain preferred solvents include $C_8$-$C_{18}$ alkanes or mixtures of $C_8$-$C_{18}$ alkanes, more particularly, preferred solvents include n-dodecane and mixtures of, by volume, about 50-70% n-decane and about 50-30% n-dodecane.

In certain other preferred methods of preparing salts of $B_{10}H_{10}^{2-}$, $B_9H_9^-$, $B_{11}H_{14}^-$ and/or $B_{12}H_{12}^{2-}$, a mixture of $R_4NBH_4$ and a trialkylamine borane adduct is pyrolyzed. Preferably the molar ratio of the ammonium borohydride and trialkylamine borane is between about 1:3 to about 3:1 where an equimolar ratio of ammonium borohydride and trialkylamine borane are particularly preferred. In certain preferred methods in which isotopically enriched salts of $B_{10}H_{10}^{2-}$, $B_9H_9^-$, $B_{11}H_{14}^-$ and/or $B_{12}H_{12}^{2-}$ are desirable, the $R_4NBH_4$ and/or the trialkylamine borane adduct is isotopically enriched in either $^{10}B$ or $^{11}B$.

The tetraalkylammonium salts provided by the pyrolytic methods of the invention, including salts of the $B_{10}H_{10}^{2-}$, $B_9H_9^-$, $B_{11}H_{14}^-$ and $B_{12}H_{12}^{2-}$ anions, are suitable for use as starting materials in the synthesis of a variety of large boron hydride compounds having more than about 12 boron atoms. For example, oxidation of tetraalkylammonium salts of $B_{10}H_{10}^{2-}$ in aqueous solution using an appropriate oxidants such as iron(III) trichloride results in the formation of $B_{20}H_{18}^{2-}$ salts. The $B_{20}H_{18}^{2-}$ salts are then contacted with an acid exchange resin and the free acid decomposed to produce $B_{18}H_{22}$ by the following method:

(a) providing a salt of $(B_{20}H_{18})^{2-}$;
(b) contacting the $(B_{20}H_{18})^{2-}$ salt in its free form, as a slurry in at least one non-aqueous solvent, as an aqueous solution, or as a solution in at least one non-aqueous solvent with an acid under conditions conducive to the formation of a conjugate acid of the $(B_{20}H_{18})^{2-}$ salt;
(c) removing volatile components of the solution comprising the conjugate acid of the $(B_{20}H_{18})^{2-}$ salt under conditions conducive to the degradation of at least a portion of the conjugate acid of the $(B_{20}H_{18})^{2-}$ salt;
(d) extracting the residue with hexanes or other suitable hydrocarbon solvents in which boric acid byproduct is insoluble;
(e) repeating steps (c) and (d) until no further $B_{18}H_{22}$ is produced
(f) contacting the residues with acetonitrile to dissolve any $B_{20}H_{18}^{2-}$ containing salts,
(g) repeating steps (b)-(f) at least once; and
(h) concentrating the combined hydrocarbon solutions to afford $B_{18}H_{22}$.

In certain preferred methods of preparing octadecaborane (e.g., $B_{18}H_{22}$) provided by the invention, the boric acid is isotopically enriched. That is, the boric acid is B-10 enriched boric acid or B-11 enriched boric acid.

In certain other preferred methods of preparing octadecaborane (e.g., $B_{18}H_{22}$) provided by the invention, the step of preparing $R_4NBH_4$ comprises contacting about equal molar amounts of sodium borohydride and $R_4NX$. In certain preferred methods, the sodium borohydride is isotopically enriched. That is, the sodium borohydride is B-10 enriched sodium borohydride or B-11 enriched sodium borohydride. In certain other preferred methods, the sodium borohydride is prepared and used in situ. One, non-limiting method of preparing sodium borohydride contemplated for use in the instant method comprises contacting the borate ester and $NaAlH_4$ in an ethereal solvent at a temperature of from about 65° C. to about 135° C. Preferred ethereal solvents comprise tetrahydrofuran, diethyl ether, or mixtures of tetrahydrofuran and toluene.

In certain other preferred methods of preparing octadecaborane (e.g., $B_{18}H_{22}$) provided by the invention, the non-aqueous solvent is a nitrile, alcohol, ether or combination thereof. Certain particularly preferred non-aqueous solvents include acetonitrile or ethanol.

In certain other preferred methods of preparing octadecaborane (e.g., $B_{18}H_{22}$) provided by the invention, the extraction hydrocarbon is a $C_5$-$C_{12}$ alkane, $C_5$-$C_{10}$ cycloalkane, benzene, or alkylated benzene. Particularly preferred extraction hydrocarbons are selected from hexanes, cyclohexane, benzene, toluene or xylene.

The following non-limiting examples are illustrative of the invention. All documents mentioned herein are incorporated herein by reference.

EXAMPLE 1

Preparation of $^{10}B$ Tributylborate

A one-neck 500 mL round bottom flask having a Dean-Stark receiver and reflux condensor attached thereto was charged with $^{10}B$-boric acid (40 g), n-butanol (200 g), and toluene (about 100 mL). The mixture was heated to reflux and water was removed from the mixture by distillation of a toluene-water azeotrope. After removing the Dean-Stark receiver, the product mixture was fractionally distilled. $^{10}$B tributylborate was obtained as a fraction boiling at 226-228° C. under ambient pressure (195 g, 87% isolated yield).

EXAMPLE 2

Preparation of $^{11}$B Enriched Tributylborate

Starting with $^{11}$B enriched boric acid, $^{11}$B tributylborate was prepared according to the procedure recited in Example 1.

EXAMPLE 3

Preparation of $^{10}$B Enriched tris(2-methyl-2,4-pentanediolate)diborate

A mixture of $^{10}$B enriched boric acid, 2-methyl-2,4-pentanediol, and toluene were combined in a 1:1.5:1 molar ratio in a reactor having a Dean-Stark Receiver and a condenser attached thereto. The reaction mixture was heated to reflux and water generated by the condensation reaction was removed as a toluene-water azeotrope. The mixture was heated until the three molar equivalents of water had been collected in the Dean-Stark trap. The reaction mixture comprises the product $^{10}$B Enriched tris(2-methyl-2,4-pentanediolate)diborate in essentially quantitative yield and toluene. The mixture may be contacted directly with metal aluminum hydride in the next step of the metal borohydride synthesis. Alternatively, the $^{10}$B Enriched tris(2-methyl-2,4-pentanediolate)diborate may be purified by toluene removal under a reduced pressure atmosphere.

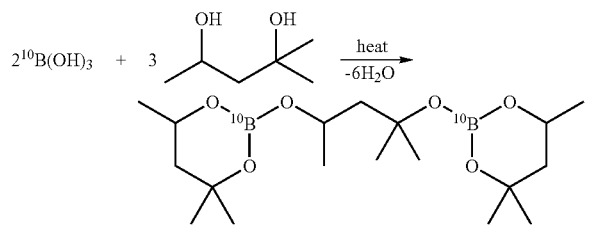

EXAMPLE 4

Preparation of $^{11}$B Enriched tris(2-methyl-2,4-pentanediolate)diborate $^{11}$B Enriched tris(2-methyl-2,4-pentanediolate)diborate was prepared by the method of Example 3 wherein $^{11}$B enriched boric acid was used in place of $^{10}$B boric acid.

EXAMPLE 5

Preparation of $^{11}$B Enriched Sodium Borohydride

A five liter 3-neck flask equipped with an overhead stirrer and a reflux condenser was charged with anhydrous tetrahydrofuran (1 L) and anhydrous diethyl ether (700 mL) under an argon atmosphere. Sodium aluminum hydride (105 g, ca 86% purity,1.77 mole) was added to the reaction flask and a pressure equalized addition funnel was charged with $^{11}$B enriched tributylborate (427 mL, 1.57 mole) which was prepared in Example 2. The borate was added dropwise to a stirred reaction mixture and the reaction mixture was gradually heated to reflux and maintained at reflux for several hours. Upon cooling, crude solid $^{11}$B enriched sodium borohydride was filtered under a positive pressure of argon atmosphere, the solid was washed with dry toluene to remove aluminum butoxide byproducts, and the toluene removed by filtration under a positive pressure argon atmosphere. The toluene wash and filtration process is repeated as necessary to remove residual aluminum butoxide byproducts. Yield: 55.5 g, 1.46 mole, 93.1%. The only boron species observed by $^{11}$B NMR spectroscopy is the resonance corresponding to $^{11}$BH$_4$ (a 1:4:6:4:1 quintet centered at −37 ppm). If necessary, $^{11}$B enriched Na$^{11}$BH$_4$ can be further purified by recrystallization from diglyme or by extraction with liquid ammonia. The resulting products retain the isotopic purity of the starting $^{11}$B enriched $^{11}$B(OH)$_3$, and $^{11}$B enriched tributylborate. This preparation has been successfully scaled up to multi-kilogram quantities without loss of product quality.

EXAMPLE 7

Preparation of Tetraethylammonium Borohydride

NaBH$_4$, (261.4 g, 6.9 moles) is weighed into a 4 L erlenmeyer flask and dissolved into 2.3 L of the prepared basic methanol solution. 600 mL of the basic methanol is used to dissolve Et$_4$NBr (1452.5 g, 6.9 moles) in a 2 L Erlenmeyer flask. To this solution is added anhydrous MgSO$_4$ (158.4 g, 1.3 moles). With rapid stirring the Et$_4$NBr solution is slowly added to the NaBH$_4$ solution to produce an immediate white precipitate of NaBr. The solution is stirred for 3 hours at room temperature. Any remaining solid is removed by vacuum filtration and the filtrate is collected and the methanol removed to give a white solid. After removing any remaining methanol under vacuum, the solid is extracted with CH$_2$Cl$_2$ (2×1.7 L). The CH$_2$Cl$_2$ extracts are combined, dried over MgSO$_4$ and filtered. The filtrate is collected and the CH$_2$Cl$_2$ removed on a rotary evaporator until most of the CH$_2$Cl$_2$ is removed and white crystalline solid begins to form. CH$_2$Cl$_2$ recovered in the receiving bulb is saved for future use. Diethylether (1.4 L) is added to the CH$_2$Cl$_2$ solution to precipitate Et$_4$NBH$_4$ as a white microcrystalline powder. After cooling to 0° C. the Et$_4$NBH$_4$ is isolated by filtration and dried under vacuum. Yield: 910.2 g, 6.3 moles, 90.9%. The preparation is successfully used in the synthesis of $^{11}$B— or $^{10}$B-enriched product.

EXAMPLE 8

Preparation of Tetraethylammonium Decahydrodecaborate

Et$_4$NBH$_4$ (1000.0 g, 6.9 moles) is weighed into a beaker and then transferred into a 5 L 3-necked round bottom flask using a powder funnel. The flask is set into a 5 L heating mantle. A 60:40 mixture of n-decane:n-dodecane (2.5 L) is added to the flask through a funnel. The center neck of the flask is equipped with a Trubore© glass bearing and glass stir rod with 24 mm×130 mm blade. The stir rod is inserted into the chuck of an overhead mixer. To one side neck is added a Claisen thermometer adapter fitted with a thermometer and a stopcock with valve used as an argon inlet. To the third neck is added a condenser equipped with a tubing adapter. The tubing adapter is attached to two isopropanol bubblers. To the inlet is attached an argon hose and the entire apparatus is thoroughly purged with argon. After the purge the argon inlet valve is shut and the reaction mixture heated to reflux (185° C.) with stirring. The reflux is maintained for 16 hours. After 16 h the heating mantle is turned off mixture cooled under argon and the white precipitate is vacuum filtered. Any remaining reaction solvent in the crude solid is removed through washing with hexanes. The crude solid is dissolved into acetonitrile (1 l), the solution heated to 40° C. and air bubbled through for 30 minutes. The solution is cooled and any precipitate is filtered off. Acetonitrile is removed and the residue recrystallised from a water-isopropanol mixture. Yield of $(Et_4N)_2B_{10}H_{20}$: 124.9 g, 0.33 moles, 48.1%.

EXAMPLE 9

Preparation of Octadecaborane $(NEt_4)_2B_{20}H_{18}$ (10.8 g, 21.8 mmol) was dissolved into a solution comprising 40 mL of acetonitrile and 5 mL of water and then stirred over 54.0 g of acidic exchange resin for 24 hours. The resin was filtered off and washed thoroughly with acetonitrile. The filtrate and washings were combined and concentrated to a yellow oil. The oil was placed under vacuum until a hard solid formed (~5 days) and then extracted with 100 mL of hexanes. Removal of hexanes left pale yellow $B_{18}H_{22}$ (2.0 g, 0.92 mmol). The residue left over from the hexane extraction was exposed to vacuum and extracted a second time to remove more $B_{18}H_{22}$. Total yield: 2.8 g, 12.9 mmol, 59.2%.

EXAMPLE 10

Preparation of $^{11}$B-enriched Octadecaborane $^{11}$B enriched $(NEt_3H)_2B_{20}H_{18}$ (17.4 g, 35.2 mmol) was dissolved into 50 mL of acetonitrile and 5 mL of $H_2O$. The solution was placed on a column containing 500 g of acidic exchange resin and allowed to sit for 18 hours. The solution was eluted from the column and the resin rinsed thoroughly with acetonitrile. The eluant and washings were combined and passed through a second column over 2 hours. Acetonitrile was removed to form a thick slurry containing yellow crystals of $H_2B_{20}H_{18} \cdot xH_2O$. The slurry was exposed to vacuum over 10 days to produce a yellow solid. To the solid was added 100 mL of $H_2O$ and 100 mL of hexanes and the mixture was stirred for 3 hours. The hexane layer was separated from the water layer, dried over $K_2CO_3$ and filtered. After removal of hexanes $^{11}$B enriched $B_{18}H_{22}$ was left as a pale yellow powder (3.5 g, 16.1 mmol, 45.9%). $^{11}$B enrichment was determined to be that of the starting boric acid (>98.6% $^{11}$B isotopic enrichment).

The invention has been described in detail with reference to preferred embodiments thereof. However, it will be appreciated that those skilled in the art, upon consideration of the disclosure, may make modifications and improvements within the spirit and scope of the invention.

All of the patents and publications cited herein are hereby incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of preparing $B_{18}H_{22}$ from boric acid comprising the steps of:
   (a) preparation of borate ester from boric acid and a primary, secondary, or tertiary alcohol;
   (b) reducing the borate ester with $NaAlH_4$ or NaH to form $NaBH_4$;
   (c) preparing $R_4NBH_4$ from $NaBH_4$ and $R_4NX$ either in situ or after isolation of $NaBH_4$, wherein R is a hydrocarbon and X is an anion;
   (d) pyrolysis of solid $R_4NBH_4$ at about 185° C. to form $B_{10}H_{10}^{2-}$;
   (e) oxidation of $B_{10}H_{10}^{2-}$ to give $B_{20}H_{18}^{2-}$;
   (f) contacting a solution of $B_{20}H_{18}^{2-}$ with acidic cation exchange resin;
   (g) decomposing the resultant acid to give $B_{18}H_{22}$;
   (h) extracting the residue with solvent in which boric acid byproduct is insoluble;
   (i) repeating steps (g) and (h) until no further $B_{18}H_{22}$ is produced;
   (j) contacting the residues with solvent to dissolve any $B_{20}H_{18}^{2-}$ containing salts and excluding boric acid byproduct;
   (k) repeating steps with (f)-(j) at least once; and
   (l) concentrating the combined hydrocarbon solutions to afford $B_{18}H_{22}$.

2. The method of claim 1, wherein the boric acid is B-10 enriched boric acid.

3. The method of claim 1, wherein the boric acid is B-11 enriched boric acid.

4. The method of claim 1, wherein the step of preparing $R_4NBH_4$ comprises contacting about equal molar amounts of sodium borohydride and $R_4NX$.

5. The method of claim 4, wherein the sodium borohydride is B-10 enriched sodium borohydride.

6. The method of claim 4, wherein the sodium borohydride is B-11 enriched sodium borohydride.

7. The method of claim 4, wherein the sodium borohydride prepared in step (b) is used in situ.

8. The method of claim 1, wherein the step of preparing $NaBH_4$ comprises contacting the borate ester and $NaAlH_4$ in an ethereal solvent at a temperature of from about 65° C. to about 135° C.

9. The method of claim 8, wherein the borate ester is a B-10 enriched borate ester.

10. The method of claim 8, wherein the borate ester is B-11 enriched borate ester.

11. The method of claim 8, wherein the ethereal solvent is tetrahydrofuran.

12. The method of claim 8, wherein the ethereal solvent further comprises toluene as a co-solvent.

13. The method of claim 11, wherein the ethereal solvent further comprises toluene as a co-solvent.

14. A method of preparing $B_{18}H_{22}$ from boric acid, comprising:
   (a) preparation of borate ester from boric acid and an alcohol;
   (b) reducing the borate ester to form $NaBH_4$;
   (c) preparing $R_4NBH_4$ from $NaBH_4$ and $R_4NX$, wherein R is a hydrocarbon and X is an anion;
   (d) pyrolysis of solid $R_4NBH_4$ to form $B_{10}H_{10}^{2-}$;
   (e) oxidation of $B_{10}H_{10}^{2-}$ to give $B_{20}H_{18}^{2-}$;
   (f) contacting a solution of $B_{20}H_{18}^{2-}$ with acidic cation exchange resin;
   (g) decomposing the resultant acid to give $B_{18}H_{22}$;
   (h) extracting the residue with solvent in which boric acid byproduct is insoluble;
   (i) repeating steps (g) and (h) until substantially no further $B_{18}H_{22}$ is produced;
   (j) contacting the residues with solvent to dissolve any $B_{20}H_{18}^{2-}$ containing salts and excluding boric acid byproduct.

15. The method of claim 14, wherein steps with (f)-(j) are repeated at least once.

* * * * *